United States Patent [19]  [11] 4,339,427
Goldstein et al.  [45] Jul. 13, 1982

[54] RADIOIMMUNOASSAY OF THYMOSINα

[75] Inventors: Allan L. Goldstein, Washington, D.C.; John E. McClure, Fairfax, Va.; Su-Sun Wang, Belmont, Calif.

[73] Assignees: Hoffmann-la Roche Inc.; George Washington University, both of Nutley, N.J.

[21] Appl. No.: 139,944

[22] Filed: Apr. 14, 1980

[51] Int. Cl.³ .................... G01N 33/56; A61K 43/00; C07G 7/00
[52] U.S. Cl. .................................. 424/1; 260/112 R; 424/12
[58] Field of Search ............................ 424/1, 12, 177; 260/112 R, 112.5 R, 112 B; 23/230 B

[56] References Cited

U.S. PATENT DOCUMENTS 4,264,571 4/1981 Goldstein et al. ...................... 424/1

OTHER PUBLICATIONS

An Introduction to Radioimmunoassay and Related Techniques, T. Chard, North Holland Publishing Co., New York, 1978, p. 353.

Primary Examiner—Christine M. Nucker
Attorney, Agent, or Firm—Jon S. Saxe; George M. Gould; Peter R. Shearer

[57] ABSTRACT

An improved radioimmunoassay for the polypeptidic thymic hormone thymosin$\alpha_1$ is described. The assay employs a radiolabelled [Tyr¹]-thymosin$\alpha_1$ or [Tyr¹]-desacetylthymosin$\alpha_1$ as probe and an affinity purified thymosin$\alpha_1$ antibody of improved selectivity.

10 Claims, No Drawings

RADIOIMMUNOASSAY OF THYMOSINα

The invention described herein was made partly in the course of work under a grant or award from the Department of Health, Education and Welfare.

BACKGROUND OF THE INVENTION

Thymosin $\alpha_1$ is a heat stable, acidic polypeptide composed of 28 amino acid residues. This thymic hormone has been isolated from calf thymus thymosinfraction 5 and its amino acid sequence determined. Thymosin $\alpha_1$ is one of several polypeptides present in thymosin fraction 5 which participate in the regulation, differentiation and function of thymic dependent lymphocytes (T-cells). The isolation, characterization and use of thymosin $\alpha_1$ is described in greater detail in U.S. Pat. No. 4,079,127.

An immunoassay for a polypeptide hormone of the thymus known as thymopoietin or thymin is disclosed in U.S. Pat. No. 4,055,633. In particular, this patent discloses a radioimmunoassay for thymopoietin utilizing an antibody elicited by an immunogen comprising purified thymopoietin covalently coupled to an immunogenic carrier material such as bovine gamma globulin using glutaraldehyde as the coupling agent. The labelled antigen used in the assay is preferably $^{125}$I thymopoietin.

It should be noted that thymopoietin is totally non-analogous to thymosin $\alpha_1$ in structure, amino acid composition and sequence, biological activity profile, physical properties and immunological properties.

A radioimmunoassay for a partially purified thymosin fraction, i.e., thymosin fraction 6, which is now known to contain a mixture of a number of polypeptides, is reported by Schulof et al., Fed. Proc. 32,962 (1973). See alsoGoldstein et al., Fed. Proc. 33,2053 (1974).

U.S. patent application Ser. No. 4,971 filed Jan. 22, 1979, now U.S. Pat. No. 4,264,571 describes a radioimmunoassay for thymosin $\alpha_1$. This assay employs an antibody elicited by an immunogen comprising thymosin $\alpha_1$ covalently linked to hemocyanin bya glutaraldehyde linking group. $^{125}$I-thymosin $\alpha_1$ was used as the label and was prepared by treatment with Bolton-Hunter reagent. The assay procedure utilized the double antibody method to achieve precipitation of the immune complex. Goat anti-rabbit gamma globulin was used as the second antibody.

Desacetylthymosin $\alpha_1$ was disclosed by Merrifield et al. during the Alan E. Pierce Award Lecture on Solid Phase Peptide Sythesis at the 6th American Peptide Symposium on June 20, 1979 which was published in December 1979.

DESCRIPTION OF THE INVENTION

The present invention relates to an improved radioimmunoassay for thymosin $\alpha_1$. The improvements in such assay involve the use of an antibody which has been made more specific to thymosin $\alpha_1$ by treating it with a bovine kidney fraction 5 to remove cross reacting impurities and also by utilizing a radiolabelled product derivedfrom a synthetic, tyrosine-containing analog of thymosin $\alpha_1$.

The use of [Tyr$^1$]-thymosin $\alpha_1$ for the radioiodination substrate used in preparing the radioactive tracer employed in the radioimmunoassay represents a distinct improvement in previous methodology. As opposed to the Bolton-Hunter radiolabelling procedure or chemical modification with non-labelled Bolton-Hunter reagent followed by classical radiolabelling techniques, the [Tyr$^1$]-thymosin $\alpha_1$ provides a labelled product of high specific activity which retains a high degree of immunoreactivity. The tyrosine residue incorporated into the primary sequence at the aminoterminal end of the peptide presents less steric hindrance to binding with antibody than would be attained with the addition of the aromatic ring structure at sites internal and perhaps nearer to the antigenic determinant. Additionally, it has been found that the [Tyr$^1$]-thymosin $\alpha_1$ can be labelled more uniformly and reproducibly than can the natural thymosin $\alpha_1$ with Bolton-Hunter reagent. Exclusive use of chemically synthesized peptides gives to the assay a high degree of specificity since there is no possibility of contamination of the preparation with compounds which could co-purify from the tissue of origin.

The immunogen utilized to prepare the antibody for the instant assay is readily obtained by covalently bonding thymosin $\alpha_1$ to a conventional immunological carrier material. The source of the thymosin $\alpha_1$ is not narrowly critical to the practice of the invention. Suitable thymosin $\alpha_1$ can be derived from fraction 5 obtained from various mammalian sources. Thus, for example, thymosin $\alpha_1$ obtained from human, bovine, sheep or porcine fraction 5 preparations can be employed. This is possible due to the homology of amino acid sequences of thymosin $\alpha_1$ derived from these various mammalian species.

Alternatively and preferably, thymosin $\alpha_1$ obtained by peptide synthesis procedures now known in the art can be employed. Thus, for example, the synthesis of thymosin $\alpha_1$ by both solid phase and solution phase procedures isdescribed in detail in U.S. Pat. No. 4,148,788.

As used herein the term "immunogenic carrier material" is meant to include those materials which have the property of independently eliciting an immunogenic response in a host animal and which can be covalently coupled to thymosin $\alpha_1$ either directly via the formation of peptide or ester bonds between free carboxyl, amino or hydroxyl groups in thymosin $\alpha_1$ and corresponding groups on the immunogenic carrier material or alternatively by bonding through a conventional bifunctional linking group.

The covalent coupling of thymosin $\alpha_1$ to the immunogenic carrier material can be carried out in a manner well known in the art. Thus, for example, for direct covalent coupling it is possible to utilize a carbodiimide, most preferably dicyclohexylcarbodiimide or 1-ethyl-3-(3-dimethylaminopropyl)carbodiimide as coupling agent. In such direct coupling it is desirable to utilize a slightly acidic reaction medium for this step, e.g., a medium having a pH in the range of from about 3 to 6.5, most preferably in the range of from about 4 to 6.5.

A suitable bifunctional linking group for effecting coupling is a $C_{2-7}$ dialkanal such as glutaraldehyde. Such coupling in this alternate embodiment can conveniently be carried out using the conditions described by S. Avrameas, Immunochemistry 6, 43 (1969).

The resulting immunogen can be utilized without further purification or, although not necessary, after dialysis to remove any unreacted thymosin $\alpha_1$ and coupling reagents.

Suitable carrier materials which can be used in the preparation of the immunogens of the instant invention include proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein utilized in the preparation of an immunogen of the instant invention is not critical. Examples of suitable proteins include mammalian serum proteins such as, for example, human gamma globulin, human serum albumin, bovine serum albumin, methylated bovine serum albumin, rabbit serum albumin, bovine gamma globulin and equine gamma globulin or non-mammalian proteins such as hemocyanin, particularly Keyhole Limpet hemocyanin (KLH). Other suitable proteins will be suggested to one skilled in the art.

The immunogen of the present invention may be utilized to induce formation of antibodies specific to thymosin $\alpha_1$ in host animals by injecting the immunogen in such a host, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with thymosin $\alpha_1$. Due to a high level of homology between the thymosin $\alpha_1$ sequences derived from various mammalian species, it is possible to utilize antibodies raised against one species of thymosin $\alpha_1$ to assay for thymosin $\alpha_1$ of other mammalian species.

[Tyr$^1$]-thymosin $\alpha_1$ used as the substrate for radioiodination is a novel compound and can be conveniently prepared using solid phase peptide procedures analogous to those employed in the synthesis of thymosin $\alpha_1$ such as is described in the aforementioned U.S. Pat. No. 4,148,788 with the exception that the last amino acid added is tyrosine. The resulting peptide is then treated with an acetylating agent such as acetic anhydride or acetic acid to provide the desired N-terminal acetyl group.

In an alternative embodiment the peptide is cleaved from the resin without acetylation so as to provide [Tyr$^1$]-desacetylthymosin $\alpha_1$ which upon radioiodination provides a radiolabel of equivalent utility as the compound derived from [Tyr$^1$]-thymosin $\alpha_1$.

While radioiodinated [Tyr$^1$]-thymosin $\alpha_1$ or [Tyr$^1$]-desacetylthymosin $\alpha_1$ are reagents of preference in the radioimmunoassay, it is possible to employ other radiolabelled reagents. Such reagents include [Tyr$^1$]-thymosin $\alpha_1$ or [Tyr$^1$]-desacetylthymosin $\alpha_1$ labelled with tritium ($^3$H) or carbon 14 ($^{14}$C). Tritium can be introduced into such reagents by use of isotopic exchange procedures known in the art. The production of $^{14}$C-[Tyr$^1$]-thymosin $\alpha_1$ or $^{14}$C-[Tyr$^1$]-desacetylthymosin $\alpha_1$ is readily accomplished by incorporating one or more commercially available $^{14}$C-labelled amino acids into the appropriate steps of the solid phase synthesis procedures referenced above.

Various assay methods can be employed in the practice of this invention. In one such procedure, known amounts of a sample to be assayed, the thymosin $\alpha_1$ specific antibody and the labelled thymosin $\alpha_1$ are mixed together and allowed to stand. The antibody-antigen complex is separated from the unbound reagents by procedures known in the art, i.e., by treatment with ammonium sulfate, polyethylene glycol, second antibody either in excess or bound to an insoluble support, dextran coated charcoal and the like. The concentration of labelled thymosin $\alpha_1$ is determined in either the bound or unbound phase and the thymosin $\alpha_1$ content of the sample can then be determined by comparing the level of labelled component observed to a standard curve in a manner known per se. A suitable standard curve can be obtained by mixing known amounts of thymosin $\alpha_1$ with fixed amounts of labelled thymosin $\alpha_1$ and the thymosin $\alpha_1$ specific antibody and determining the degree of binding for each such known amount.

While the treatment of thymosin $\alpha_1$ specific antibodies with bovine kidney fraction 5 has been described above, it should be noted that this represents a preferred embodiment of the invention. It is within the scope of the present invention to employ a fraction 5 derived from any mammalian organ which does not contain thymosin $\alpha_1$ producing cells. Suitable organs besides kidney include liver and brain. Other mammalian sources for such organs include camel, sheep, horses, monkey, pig, human and the like.

The present invention is further illustrated by the following examples.

EXAMPLE 1

Boc-α-benzyl-L-aspartyl benzhydrylamine resin

Benzhydrylamine resin (10 g., 0.4 mmol/g.) was stirred with 250 ml. of 25% Et$_3$N in CH$_2$Cl$_2$ for 10 minutes and then washed a few times with fresh CH$_2$Cl$_2$. It was then suspended in 240 ml. of CH$_2$Cl$_2$ and stirred with Boc-α-benzyl-L-aspartic acid (3.24 g., 10 mmol) and DCC (2.06 g., 10 mmol) for 17 hours. The amino acylated resin was collected, washed thoroughly with CH$_2$Cl$_2$, DMF and MeOH. It was dried and benzoylated with 1.5 ml. of pyridine and 1.65 ml. of benzoyl chloride in 110 ml. of CH$_2$Cl$_2$ for 15 minutes at 0° C. The resin was washed with CH$_2$Cl$_2$, MeOH to give 10.7 g. of desired material. Amino acid analysis indicated that there was 0.40 mmol/g. of aspartic acid.

EXAMPLE 2

Ac-Tyr-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn

Boc-α-benzyl-L-aspartylbenzhydrylamine resin (10 g., 4.0 mmol) was placed in a 250 ml. peptide synthesis flask and the solid phase synthesis performed with the following steps in each cycle: (1) three washings with CH$_2$Cl$_2$, (2) prewash with 50% TFA in CH$_2$Cl$_2$, (3) shake 25 minutes with 50% TFA in CH$_2$Cl$_2$, (4) three washings with CH$_2$Cl$_2$, (5) prewash with 10% Et$_3$N in CH$_2$Cl$_2$, (6) shake 10 minutes with 10% Et$_3$N in CH$_2$Cl$_2$, (7) three washings each with CH$_2$Cl$_2$, i-PrOH, CH$_2$Cl$_2$, (8) shake 120 minutes with 10 mmol each of Boc-Glu(OBzl)-OH (3.37 g.) and DCC (2.06 g.) in CH$_2$Cl$_2$, (9) three washing each with CH$_2$Cl$_2$, DMF, i-PrOH, CH$_2$Cl$_2$, (10) shake 10 minutes with 10% Et$_3$N in CH$_2$Cl$_2$, (11) three washings with CH$_2$Cl$_2$, (12) shake 30 minutes with 8 mmol each of Boc-Glu(OBzl)-OH (2.69 g.) and DCC (1.65 g.) in CH$_2$Cl$_2$, (13) three washings each with CH$_2$Cl$_2$, DMF, i-PrOH.

The synthetic cycle was repeated using the following amino acids, sequentially, one at a time in step 8 (10 mmol each) and in step 12 (8 mmol each): Boc-Ala-OH, Boc-Glu(OBzl)-OH, Boc-Glu(OBzl)-OH, Boc-Val-OH, Boc-Val-OH, Boc-Glu(OBzl)-OH, Boc-Lys(2-ClZ)-OH, Boc-Lys(2-ClZ)-OH, Boc-Glu(OBzl)-OH, Boc-Lys(2-ClZ)-OH, Boc-Leu-OH, Boc-Asp(OBzl)-OH, Boc-Lys(2-ClZ)-OH, Boc-Thr(Bzl)-OH, Boc-Thr(Bzl)-OH, Boc-Ile-OH, Boc-Glu(OBzl)-OH, Boc-Ser(Bzl)-OH, Boc-Ser(Bzl)-OH, Boc-Thr(Bzl)-OH, Boc-Asp(OBzl)-OH, Boc-Val-OH, Boc-Ala-OH, Boc-Ala-OH, Boc-Asp(OBzl)-OH, Boc-Tyr(Bzl)-OH and AcOH. On completion of the synthesis, 18.68 g. of protected peptide resin was obtained. A 6.0 g. sample of the protected peptide resin was then subjected to HF cleavage (40 ml. HF, 10 ml. anisole) at 0° for 30 minutes. After evaporation of HF (0°), the residue was stirred with 60 ml. of 10% AcOH overnight (adjusted to pH 7.0 with ammonia). The milky suspension was filtered to remove the resin and the filtrate washed several times with ether. The aqueous layer was concentrated to approximately 25 ml. and desalted on a Sephadex G-10 column (5×80 cm). Lyophilization of the material in the major peak gave 0.79 g. of crude [$Tyr^1$]-thymosin $\alpha_1$. It was then chromatographed on a DEAE-Sephadex A-25 column (2.5×90 cm) using a linear gradient of NaCl (0.0 - 0.35 M) in 0.05 M Tris.HCl (pH 8.0 ) buffer at a flow rate of 100 ml. per hour. The main peak (276 nm) was pooled, desalted on a Sephadex G-10 column (0.2 M HOAc; 2.5×90 cm) and lyophilized to give 0.17 g. of [$Tyr^1$]-thymosin $\alpha_1$. The overall yield was calculated to be 4.15% based on the aspartic acid content of Boc-$\alpha$-benzyl-aspartyl benzhydrylamine resin. The compound migrated as a single spot on silica gel thin layer electrophoresis (pH 1.9) and on acrylamide gel isoelectric focusing (pH 3.5-9.5). The amino acid composition of the product after hydrolysis in 4 N methanesulfonic acid at 110° was as follows:

|     | Calcd | 24 hr | 96 hr |
| --- | --- | --- | --- |
| Asp | 4.00 | 4.35 | 4.00 |
| Thr | 3.00 | 2.50 | 2.35 |
| Ser | 2.00 | 1.97 | 1.60 |
| Glu | 6.00 | 6.01 | 6.82 |
| Ala | 3.00 | 3.60 | 2.89 |
| Val | 3.00 | 1.72 | 2.45 |
| Ile | 1.00 | 0.86 | 0.79 |
| Leu | 1.00 | 0.96 | 0.90 |
| Tyr | 1.00 | 0.98 | 0.78 |
| Lys | 4.00 | 3.60 | 4.00 |

EXAMPLE 3 a. Preparation of antisera

Synthetic thymosin $\alpha_1$ was coupled to Keyhole Limpet Hemocyanin (KLH) by means of glutaraldehyde using the following procedure. Equivalent amounts (dry weight) of each protein, thymosin $\alpha_1$ and hemocyanin, were dissolved in 0.25 M $NaPO_4$, pH 7.0 buffer at a concentration of 2 mg/ml. Equal volumes of the protein solutions were mixed, and a volume of glutaraldehyde (25% aqueous solution) equal to 1% of the volume of the protein mixture was added. The reaction was allowed to continue for 3 hours while being stirred at room temperature. The reaction mixture was diluted in sterile saline to a final concentration of thymosin $\alpha_1$ of 100 $\mu$g/ml. The solution of coupled thymosin $\alpha_1$ was aliquoted and stored at $-20°$ C.

The mixture of products resulting from the cross-linking reactions carried out at room temperature was not fractionated or purified in any way. The thymosin $\alpha_1$ KLH conjugate was diluted with sterile normal saline and stored frozen for immunizations. Rabbits were immunized by administering 100 $\mu$g thymosin $\alpha_1$ (as the KLH conjugate) in emulsion with Freund's Complete Adjuvant at 15-20 intradermal sites on the back of each rabbit according to the method of Vaitukaitis et al., J. Clin. Endoch. 33,988 (1971). Weekly boosts of 50 $\mu$g thymosin $\alpha_1$ per animal in Freund's Incomplete Adjuvant were also administered at multiple intradermal sites. Titers of antibody against the peptide which were usable in the RIA were finally obtained following a rest period of three months, subsequent boosting with 50 $\mu$g amounts of thymosin $\alpha_1$ and bleeding of each rabbit 7-10 days following each boosting dose. Two of three rabbits have provided antiserum of relatively stable anti-thymosin $\alpha_1$ titers for over a year. Prior to use in the RIA, the antisera were absorbed with immobilized fraction 5 preparations of bovine kidney which produced antisera that provided more sensitivity and specificity in the RIA. One is able to use the antiserum at 1:10,000 final dilution before absorption, and at 1:3,000 final dilution following absorption with bovine kidney fraction 5.

b. Radioiodination of [$Tyr^1$]-thymosin $\alpha_1$

A method of radioiodination utilizing soluble lactoperoxidase was adopted because the $^{125}I$-[$Tyr^1$]-thymosin $\alpha_1$ obtained by this process retained a high degree of immunoreactivity and had a high specific activity (80–100 uCi/$\mu$g). The peptide to be iodinated was put into solution in 0.4 M sodium acetate, pH 5.6, together with lactoperoxidase (Calbiochem #427488, Grade B), $Na^{125}I$ (New England Nuclear #NEZ 033H), and $H_2O_2$. After a reaction time of 30 seconds at room temperature, the enzyme was inhibited by the addition of sodium azide. Purification of the $^{125}I$-[$Tyr^1$]-thymosin $\alpha_1$ was carried out on a solumn of Sephadex G-25 Superfine (2.5 cm ×40 cm) equilibrated with 10% aqueous acetic acid containing 0.2% ovalbumin and 0.05% $NaN_3$. The tracer typically demonstrated 80–85% binding with excess specific antibody which indicates a good retention of immunoreactivity. The tracer was diluted 1:2,000 in immunoassay buffer to provide 4,000-5,000 cpm per assay tube, which is equivalent to less than 1 pg peptide mass per assay tube.

c. RIA protocol

The buffer used for the radioimmunoassay is phosphate-buffered saline to which has been added 0.05% $NaN_3$ and 1:200 dilution of ammonium sulfate-fractionated normal rabbit serum (IgG enriched fraction) which serves as a protein to preventnon-specific binding of tracer and as a carrier in the double antibody precipitation step. Standard solutions of synthetic thymosin $\alpha_1$ or unknown serum samples are mixed with an appropriate dilution of specific antibody (a dilution is chosen which provides 20–25% binding of tracer in the absence of competing antigen) and incubated for 1 hour at 37° C. Tracer $^{125}I$-[$Tyr^1$]-thymosin $\alpha_1$ is added, the tubes are incubated for an additional 1 hour at 37° C. and finally incubated at 4° C. for 48 hours. Separation of free from bound tracer is carried out by the addition of goat anti-rabbit gamma globulin serum, incubation for 1 hour at 37° C. and finally incubation at 4° C. for 16 hours. The immunoprecipitate is pelleted by centrifugation at 2500 rpm for 20 minutes, the supernatant is aspirated and discarded, and the radioactivity in the immunoprecipitate is counted in an automatic gamma spectrometer. The counts per minute for standards and unknowns are corrected for non-specific background and compared to the total counts per minute for the reaction tubes where no competing antigen was introduced. An automatic data reduction program utilizing the four-parameter logistics method of Rodbard, Clinical Chem., 20,1255 (1974) is used for calculating potency estimates for all samples and for evaluating the performance of the RIA from run to run.

d. Results using the RIA for thymosin $\alpha_1$

The standard curve for the RIA has indicated a sensitive system has been generated for the measurement of thymosin $\alpha_1$. The minimal detectable dose (10% inhibition) is typically 8–15 pg, the $ED_{50}$ (50% inhibition) is equivalent to 130–160 pg, and the slope at inflection point (50% inhibition) is −1.0. The operating range for the assay is between 15–800 pg. The standard error for replicate determinations of most serum samples is less than 20%.

The specificity of the radioimmunoassay was investigated by assaying a number of serum proteins, hormones, preparations which have been reported to have thymic hormone activity, and additional peptides isolated from thymosin fraction 5 (Table 1). Peptides isolated from bovine fraction 5, cross-reacted negligibly in the RIA. Cross-reaction by these preparations could mean that thymosin $\alpha_1$ was co-purified with other peptides or that additional thymosin peptides share partial amino acid sequences with thymosin $\alpha_1$.

No significant cross-reactions have been detected upon assay of a wide variety of purified serum proteins and hormones. There is no cross-reactivity with synthetic FTS or with both thymopoietin II fragment 29-41 (Bachem, Inc.) and TP.5 (Ortho Pharmaceuticals). Highly purified human serum prealbumin (Syntex, Inc.) also does not compete with synthetic thymosin $\alpha_1$ in the RIA. In addition, the oncodevelopmental antigens, carcinoembryonic antigen and alpha-fetoprotein (Hoffmann-La Roche Inc.) do not cross-react in the RIA. These antigens, as well as thymosin $\alpha_1$, are found to be in high concentration in fetal serum and to decline rapidly in early life post-partum.

Cross-reactivity has been found in human serum and plasma samples which demonstrates a dose-response parallel to the standard curve. This finding is interpreted to mean that there is a thymosin $\alpha_1$-like material in the blood. Serum samples of normal children between the ages of 6 months to 15 years have been analyzed, and the data indicates that there is a definite decrease in serum thymosin $\alpha_1$ levels after birth. Although normal ranges for each decade of life have not been firmly established, measurements of adult levels indicate probable normal ranges of 0.5 to 1.5 ng/ml. When rabbit anti-thymosin $\alpha_1$ antiserum was used in an indirect immunofluorescence technique to examine normal thymus sections, there was a decrease in specific staining of epithelial cells of the thymic medulla which was most obvious from the age of puberty to old age.

The RIA has been used to measure serum thymosin $\alpha_1$ cross-reactivity in several strains of mouse. The results in mouse parallel findings in human serum in that there is a significant decrease in serum levels during the first months of life. In some individual mice, there is an apparent increase in serum thymosin $\alpha_1$ cross-reactivity with advancing age.

TABLE 1

| Protein | $ED_{50}$ - Amount of protein (ng) required to produce a 50% inhibition in RIA |
| --- | --- |
| Synthetic thymosin $\alpha_1$ | 0.40 |
| Natural thymosin $\alpha_1$ | 0.45 |
| Thymosin fraction 5 | 200 |
| TP.5 | >15,000 |
| FTS | >230,000 |
| Partially purified prealbumin (human) | 10,000 |
| Purified prealbumin (human) | >50,000 |
| Serum albumin (human) | >500,000 |
| Serum albumin (bovine) | >250,000 |
| Myoglobin (equine) | 50,000 |
| Fetuin (bovine) | >250,000 |
| CEA | >25,000 |
| Erythropoietin (human) | >160,000 |
| FSH (porcine) | 23,000 |
| Glucagon (porcine) | >500,000 |
| Insulin (porcine) | >200,000 |
| Hemocyanin (Keyhole Limpet) | >100,000 |
| Bradykinin | >50,000 |
| Transferrin (human) | >50,000 |
| Cytochrome C (equine) | >200,000 |
| Hemoglobin (human) | >200,000 |
| L—Glu—L—Ala—L—Lyr (copolymer) | >18,000 |

EXAMPLE 4

In analogy to the procedure of Example 2 the amino acids corresponding to the [Tyr$^1$]-thymosin $\alpha_1$ are synthesized on the resin and the peptide is cleaved prior to acetylation so as to yield [Tyr$^1$]-desacetylthymosin $\alpha_1$. This compound is radioiodinated following the procedures of Example 3 so as to yield $^{125}$I-[Tyr$^1$]-desacetylthymosin $\alpha_1$ and this product is used in the radioimmunoassay method of that Example to detect thymosin $\alpha_1$.

We claim:
1. [Tyr$^1$]-thymosin $\alpha_1$.
2. [Tyr$^1$]-desacetylthymosin $\alpha_1$.
3. $^{125}$I-[Tyr$^1$]-Thymosin $\alpha_1$.
4. $^{125}$I-[Tyr$^1$]-desacetylthymosin $\alpha_1$.
5. In a method for the assay of thymosin $\alpha_1$ in a sample, which method comprises mixing said sample with a known amount of labelled thymosin $\alpha_1$ and an antibody which will selectively complex with said thymosin $\alpha_1$, separating the resulting antibody-antigen complex from uncomplexed labelled thymosin $\alpha_1$, measuring the degree of binding of the said labelled thymosin $\alpha_1$ in said complex and determining the amount of thymosin $\alpha_1$ present in said sample by comparing said degree of binding to a standard curve,
the improvement which comprises utilizing as the labelled thymosin $\alpha_1$ a compound selected from $^{125}$I-[Tyr$^1$]-thymosin $\alpha_1$ and $^{125}$I-[Tyr$^1$]-desacetylthymosin $\alpha_1$.
6. The improved method of claim 5 wherein said labelled compound is $^{125}$I-[Tyr$^1$]-thymosin $\alpha_1$.
7. The improved method of claim 5 wherein said antibody comprises an antibody pretreated with a fraction 5 preparation obtained from a mammalian organ not containing thymosin $\alpha_1$ producing cells so as to obtain an antibody of enhanced sensitivity and specificity.
8. The improved method of claim 7 wherein said mammalian organ is bovine kidney.
9. In a method for the assay of thymosin $\alpha_1$ in a sample, which method comprises mixing said sample with a known amount of labelled thymosin $\alpha_1$ and an antibody which will selectively complex with said thymosin $\alpha_1$, separating the resulting antibody-antigen complex from uncomplexed labelled thymosin $\alpha_1$, measuring the degree of binding of the said labelled thymosin $\alpha_1$ in said complex and determining the amount of thymosin $\alpha_1$ present in said sample by comparing said degree of binding to a standard curve,
the improvement which comprises utilizing as said antibody an antibody pretreated with a fraction 5 preparation obtained from a mammalian organ not containing thymosin $\alpha_1$ so as to obtain an antibody of enhanced sensitivity and specificity.
10. The improved method of claim 9 wherein said labelled compound is $^{125}$I-[Tyr$^1$]-thymosin $\alpha_1$.

* * * * *